(12) United States Patent
Kuma et al.

(10) Patent No.: US 9,227,925 B2
(45) Date of Patent: Jan. 5, 2016

(54) PROCESS FOR PRODUCING ALDEHYDE COMPOUNDS

(75) Inventors: Shigetoshi Kuma, Kurume (JP);
Michiharu Sakata, Kurume (JP);
Kouichi Tokunaga, Chikugo (JP);
Chitoshi Shimakawa, Arao (JP);
Naoyuki Kakinuma, Omuta (JP);
Masayuki Furuya, Arao (JP); Mamoru Tanaka, Fukuoka (JP)

(73) Assignee: MITSUI CHEMICALS, INC., Tokyo (JP)

( * ) Notice: Subject to any disclaimer, the term of this patent is extended or adjusted under 35 U.S.C. 154(b) by 0 days.

(21) Appl. No.: 14/114,774

(22) PCT Filed: May 7, 2012

(86) PCT No.: PCT/JP2012/002987
§ 371 (c)(1),
(2), (4) Date: Oct. 30, 2013

(87) PCT Pub. No.: WO2012/153509
PCT Pub. Date: Nov. 15, 2012

(65) Prior Publication Data
US 2014/0088321 A1    Mar. 27, 2014

(30) Foreign Application Priority Data
May 9, 2011 (JP) .................... 2011-104401

(51) Int. Cl.
| | |
|---|---|
| C07C 253/30 | (2006.01) |
| C07C 263/10 | (2006.01) |
| C07C 209/26 | (2006.01) |
| C07C 209/48 | (2006.01) |
| C07C 45/29 | (2006.01) |
| C07C 209/52 | (2006.01) |
| C07C 45/49 | (2006.01) |

(52) U.S. Cl.
CPC ............... *C07C 253/30* (2013.01); *C07C 45/29* (2013.01); *C07C 45/49* (2013.01); *C07C 209/26* (2013.01); *C07C 209/48* (2013.01); *C07C 209/52* (2013.01); *C07C 263/10* (2013.01); *C07C 2102/42* (2013.01)

(58) Field of Classification Search
CPC .................................................... C07C 47/347
USPC .......................................................... 558/353
See application file for complete search history.

(56) References Cited

U.S. PATENT DOCUMENTS

| | | | |
|---|---|---|---|
| 2,956,977 A * | 10/1960 | Caldwell et al. ......... 106/170.37 |
| 3,143,570 A | 8/1964 | Caldwell et al. |
| 4,334,100 A | 6/1982 | Hagen et al. |
| 5,360,938 A | 11/1994 | Babin et al. |
| 5,840,928 A * | 11/1998 | Satoh et al. .................. 549/483 |
| 6,252,121 B1 | 6/2001 | Argyropoulos et al. |
| 6,274,774 B1 | 8/2001 | Bogdanovic et al. |
| 2009/0081086 A1 | 3/2009 | Sasaki et al. |
| 2009/0171125 A1 | 7/2009 | Shih et al. |
| 2010/0256422 A1 | 10/2010 | Fischbach et al. |
| 2010/0324339 A1 | 12/2010 | Choi et al. |

FOREIGN PATENT DOCUMENTS

| | | |
|---|---|---|
| JP | 55-89238 A | 7/1980 |
| JP | 57-193438 A | 11/1982 |
| JP | 58-21638 A | 2/1983 |
| JP | 60-72844 A | 4/1985 |

(Continued)

OTHER PUBLICATIONS

Francio et al. "Highly efficient enantioselective catalysis in supercritical carbon dioxide using the perfluoroalkyl-substituted ligand (R,S)-3-H.sup.2.F.sup.6-BINAPHOS" J. Organomet. Chem. 2001, 621, 130-142.*

(Continued)

*Primary Examiner* — Joseph Kosack
*Assistant Examiner* — Amanda L Aguirre
(74) *Attorney, Agent, or Firm* — Buchanan, Ingersoll & Rooney PC (57) ABSTRACT

A process for producing an aldehyde compound of the invention comprising: reacting a compound represented by the following formula (a1) or (a2) with a hydrogen and a carbon monoxide in a presence of a compound containing a metal belonging to Groups 8 to 10 and a phosphorous compound so as to satisfy the following conditions (1) and (2) to synthesize an aldehyde compound;

wherein the condition (1) is that a content of a metal included in the compound containing a metal belonging to Groups 8 to 10 is 0.01 ppmmol to 300 ppmmol with respect to 1 mol of the compound represented by the formula (a1) or (a2), and wherein the condition (2) is that a molar ratio represented by the phosphorous compound (mol)/the metal (mol) is 100 or more;

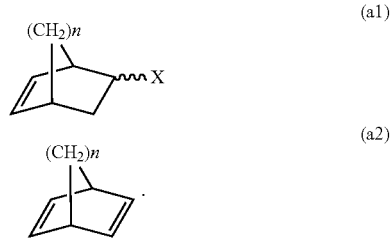

17 Claims, 3 Drawing Sheets

(56) References Cited

FOREIGN PATENT DOCUMENTS

| | | |
|---|---|---|
| JP | 4-33969 A | 2/1992 |
| JP | 7-502488 A | 3/1995 |
| JP | 11-80067 A | 3/1999 |
| JP | 2002-511055 A | 4/2002 |
| JP | 2003-505438 A | 2/2003 |
| JP | 2003-286241 A | 10/2003 |
| JP | 2006-282640 A | 10/2006 |
| JP | 2008-31125 A | 2/2008 |
| JP | 2010-180142 A | 8/2010 |
| JP | 2010-538818 A | 12/2010 |
| JP | 2011-503018 A | 1/2011 |
| KR | 2002-0039324 A | 5/2002 |
| KR | 2007-0116927 A | 12/2007 |
| WO | WO 01/07382 A3 | 2/2001 |
| WO | WO 0107382 A2 * | 2/2001 |

OTHER PUBLICATIONS

Kannoki et al. "Method for Manufacturing Formylnorbornane Containing a Polar Functional Group" JP 60-072844 (Apr. 24, 1985) English Translation by the McElroy Translation Company, USPTO, Washington, DC (Nov. 2014).*
Extended European Search Report issued in corresponding European application No. 12782970, mailed Aug. 21, 2014 (8 pages).
International Search Report (PCT/ISA/210) mailed on Aug. 7, 2012, by the Japanese Patent Office as the International Searching Authority for International Application No. PCT/JP2012/002987.
Office Action issued in corresponding Korean Patent Application No. 10-2013-7028648 on Apr. 29, 2015 (8 pages).

* cited by examiner

PROCESS FOR PRODUCING ALDEHYDE COMPOUNDS

TECHNICAL FIELD

The present invention relates to a process for producing aldehyde compounds, a process for producing amine compounds and a process for producing isocyanate compounds in which an aldehyde compound obtained by the above process is used.

BACKGROUND ART

As processes for producing aldehyde compounds in which a norbornene compound is used, for example, processes described in Patent Documents 1 to 3 are known.

Patent Documents 1 to 3 disclose processes in which hydroformylation of cyan norbornene is caused in the presence of a catalyst using a $H_2$/CO gas mixture, thereby producing formyl cyan norbornene. Patent Documents 1 and 2 disclose examples in which a compound containing a metal is used as the catalyst. Meanwhile, a rhodium complex is preferably used as the catalyst since a target compound can be highly selectively obtained and a reaction pressure can be suppressed at a low level.

Patent Document 1 describes that a content of the catalyst can be set to 0.1 weight % to 10 weight % with respect to that of cyan norbornene. Patent Document 2 describes that it is possible to set a catalyst concentration to 0.5 mmol/l to 10 mmol/l and to use triaryl phosphine in a range of 3 mol to 300 mol with respect to 1 mol of rhodium.

Patent Document 4 discloses a process in which hydroformylation of an olefin compound is caused in the presence of a transition metal catalyst and a trivalent phosphoric compound using a $H_2$/CO gas mixture. In addition, regarding a content of the metal catalyst, it is described that a content of free metal is 10 ppm to 1000 ppm in terms of a weight or volume of a catalyst composition.

Patent Document 5 describes metal ligand complex catalysts, and mentions rhodium as a metal and an organic phosphorous ligand as a ligand. Regarding use amounts thereof, it is described that a metal concentration is in a range of approximately 1 ppm to 10,000 ppm and a molar ratio of the ligand to the metal is 1:1 to 200:1 in terms of an equivalent amount of free metal.

In addition, Patent Documents 6 and 7 disclose processes in which hydroformylation of a chain-like olefin compound is caused, thereby producing an aldehyde compound.

Patent Document 6 describes hydroformylation of 7-octenal is caused in the presence of a rhodium catalyst and bisphosphite in Examples. It is described that approximately 3 ppm mol of rhodium is used with respect to 1 mol of 7-octenal, and a molar ratio of rhodium atoms to phosphorous atoms is 1/20. Meanwhile, Patent Document 6 describes in Paragraph 0084 that a content of bisphosphite is preferably 2 mol to 1000 mol with respect to 1 mol of a metal in terms of a phosphorus atom, and, in a case in which the content exceeds 1000 mol, there is a tendency of a reaction rate becoming extremely small.

In addition, Patent Document 7 describes an example in which hydroformylation of cyclohexene is caused in the presence of 3 ppm of rhodium in Examples.

RELATED DOCUMENT

Patent Document

[Patent Document 1] Japanese Unexamined Patent Publication No. 57-193438
[Patent Document 2] Japanese Unexamined Patent Publication No. 60-72844
[Patent Document 3] U.S. Pat. No. 3,143,570
[Patent Document 4] PCT Japanese Translation Patent Publication No. 2010-538818
[Patent Document 5] PCT Japanese Translation Patent Publication No. 2003-505438
[Patent Document 6] Japanese Unexamined Patent Publication No. 2008-031125
[Patent Document 7] PCT Japanese Translation Patent Publication No. 2011-503018

DISCLOSURE OF THE INVENTION

In recent years, an used amount of rare metals have increased in accordance with development of technologies, and there have been problems of depletion of rare metal resources and an increase in costs. Therefore, there has been a broad demand for reduction of the use amount and effective use of so-called rare metals.

However, in a hydroformylation reaction of a norbornene compound, for example, cyan norbornene, when an amount of a metal included in a compound containing a metal which is a catalyst with respect to a substrate decreases, there is a problem with productivity such as a decrease in a yield due to a decrease in a reaction rate or the reaction unable to proceed. That is, the reduction of the amount of a metal included in a compound containing a metal which is a catalyst has a trade-off relationship with improvement of productivity, and, hitherto, there has been no established process for reducing an amount of metal in the hydroformylation reaction of a norbornene compound.

Meanwhile, regarding a technical level of the related art in the hydroformylation reaction of a cyan norbornene compound, an amount of a metal with respect to a substrate is 55 ppm as described in Example 5 in Patent Document 1. However, selectivity was as low as 87.2%, which created a need for improvement.

That is, an object of the invention is to establish techniques that can reduce the use amount of rare metals and effectively use rare metals while maintaining the same productivity as in a case of traditional used amount of metals.

In order to solve the above problems, the present inventors thoroughly studied processes for reducing an amount of a metal included in a compound containing a metal, and found that, in a case in which a phosphorous compound which can be used as a ligand that forms a metal complex is significantly excessively added, surprisingly, a reaction rate does not decrease, an aldehyde compound can be obtained at a high yield, and the productivity does not decrease even when the amount of the metal is reduced.

The invention can be illustrated as follows.
[1] A process for producing aldehyde compounds comprising:
reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2);
wherein the condition (1) is that a content of a metal included in the compound containing a metal belonging to Groups 8 to 10 is 0.01 of ppm mol to 300 ppm mol with respect to 1 mol of the compound represented by the following formula (a1) or (a2), and
wherein the condition (2) is that a molar ratio represented by the phosphorous compound (mol)/the metal (mol) is 100 or more, wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2.

[2] The process for producing aldehyde compounds described in [1], the compound containing a metal belonging to Groups 8 to 10 is a rhodium compound, a cobalt compound, a ruthenium compound or an iron compound.

[3] The process for producing aldehyde compounds described in [1] or [2], the compound containing a metal belonging to Groups 8 to 10 is a rhodium compound.

[4] The process for producing aldehyde compounds described in any one of [1] to [3], the compound represented by the formula (a1) is used, and the compound is represented by the following formula (1);

wherein, in the formula (1), X is the same as in the formula (a1).

[5] The process for producing aldehyde compounds described in any one of [1] to [4], the phosphorous compound is a trivalent phosphorous compound.

[6] The process for producing aldehyde compounds described in any one of [1] to [5], the reacting step is carried out under solventless condition.

[7] A process for producing amine compounds comprising:
reacting the aldehyde compound obtained using the process described in any one of [1] to [6] with an ammonia, and reacting with a hydrogen in a presence of a catalyst.

[8] A process for producing isocyanate compounds comprising:
reacting the amine compound obtained using the process described in [7] with a carbonylating agent.

[9] A process for producing amine compounds comprising:
reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2) to synthesize an aldehyde compound; and
reacting the aldehyde compound with an ammonia, and reacting with a hydrogen in a presence of a catalyst;
wherein the condition (1) is that a content of a metal included in the compound containing a metal belonging to Groups 8 to 10 is 0.01 ppm mol to 300 ppm mol with respect to 1 mol of the compound represented by the following formula (a1) or (a2), and
wherein the condition (2) is that a molar ratio represented by the phosphorous compound (mol)/the metal (mol) is 100 or more, wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2.

[10] The process for producing amine compounds described in [9], the compound containing a metal belonging to Groups 8 to 10 is a rhodium compound, a cobalt compound, a ruthenium compound or an iron compound.

[11] The process for producing amine compounds described in [9] or [10], the compound containing a metal belonging to Groups 8 to 10 is a rhodium compound.

[12] The process for producing amine compounds described in any one of [9] to [11], the compound represented by the formula (a1) is used, and the compound is represented by the following formula (1);

wherein, in the formula (1), X is the same as in the formula (a1).

[13] A process for producing isocyanate compounds comprising:
reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2) to synthesize an aldehyde compound;
reacting the aldehyde compound with an ammonia, and reacting with a hydrogen in a presence of a catalyst to synthesize an amine compound; and
reacting the amine compound with a carbonylating agent;
wherein the condition (1) is that a content of a metal included in the compound containing a metal belonging to Groups 8 to 10 is 0.01 of ppm mol to 300 ppm mol with respect to 1 mol of the compound represented by the formula (a1) or (a2), and
wherein the condition (2) is that a molar ratio represented by the phosphorous compound (mol)/the metal (mol) is 100 or more, (a1)

(a2)

wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2.

[14] The process for producing isocyanate compounds described in [13], the compound containing a metal belonging to Groups 8 to 10 is a rhodium compound, a cobalt compound, a ruthenium compound or an iron compound.

[15] The process for producing isocyanate compounds described in [13] or [14], the compound containing a metal belonging to Groups 8 to 10 is a rhodium compound.

[16] The process for producing isocyanate compounds described in any one of [13] to [15], the compound represented by the formula (a1) is used, and the compound is represented by the following formula (1);

(1)

wherein, in the formula (1), X is the same as in the formula (a1).

Meanwhile, the "phosphorous compound" in the invention refers to a phosphorous compound that can form a complex with a compound containing a metal. The phosphorous compound includes phosphorous compounds in a complex state with a compound containing a metal, and free phosphorous compounds.

In addition, in the invention, in a case in which a substance B is used in an amount of $1 \times 10^{-6}$ mol with respect to 1 mol of a substance A, the amount of the substance B is expressed by 1 ppm mol.

According to the process for producing aldehyde compounds of the invention, an amount of a metal can be reduced, and productivity is excellent based on no decrease of a reaction rate, and, furthermore, aldehyde compounds can be obtained at a high yield. Since the process for producing amine compounds and the process for producing isocyanate compounds of the invention include the process for producing aldehyde compounds as a single step, an amount of a metal can be reduced, and, furthermore, the productivity and yield of aldehyde compounds are excellent. Thereby, the productivity and yield of a target compound are also excellent. As such, according to the invention, it is possible to provide techniques that can reduce the use amount of rare metals and effectively use rare metals.

BRIEF DESCRIPTION OF THE DRAWINGS

The above object, other objects, characteristics and advantages is further clarified using preferable embodiments described below and the following accompanying drawings.

DESCRIPTION OF EMBODIMENTS

Hereinafter, a process for producing aldehyde compounds of the present embodiment is described, a process for producing amine compounds and, subsequently, a process for producing isocyanate compounds is described.

<Process for Producing Aldehyde Compounds>

The process for producing aldehyde compounds of the embodiment includes a step for reacting a compound represented by the following formula (a1) or (a2) with a hydrogen and a carbon monoxide in a presence of a compound containing a metal belonging to Groups 8 to 10 and a phosphorous compound.

(a1)

(a2)

In the formula (a1), X represents a hydrogen atom, a cyano group, an aldehyde group or —CH=NR group, and R represents a hydrogen atom, an alkyl group having 1 to 6 carbon atoms or an aryl group having 6 to 20 carbon atoms. X is preferably a cyano group or an aldehyde group, and more preferably a cyano group. In the formula (a1) and the formula (a2), n represents 0, 1 or 2, is preferably 0 or 1, and more preferably 1.

Meanwhile, the compound represented by the formula (a1) may be any one of an endo compound or an exo compound, or may be a mixture having endo and exo compounds at an arbitrary ratio.

Specific examples of the compound represented by the formula (a1) include the following compounds.

(1) Examples of compounds with n=0 include cyclohexene, 4-cyano-1-cyclohexene, 3-cyclohexene-1-carboxyaldehyde and 4-iminomethyl-1-cyclohexane.

(2) Examples of compounds with n=1 include bicyclo[2.2.1]-5-heptene, bicyclo[2.2.1]-5-heptene-2-carbonitrile, bicyclo[2.2.1]-5-heptene-2-carboxyaldehyde and bicyclo[2,2,1]-5-heptene-2-ylmethanamine.

(3) Examples of compounds with n=2 include bicyclo[2,2,2]-5-octene, bicyclo[2,2,2]-5-octene-2-carbonitrile, bicyclo[2,2,2]-5-octene-2-carboxyaldehyde and bicyclo[2,2,2]-5-heptene-2-ylmethanamine.

Specific examples of the compound represented by the formula (a2) include the following compounds.

(1) Examples of compounds with n=0 include 1,3-cyclohexadiene.

(2) Examples of compounds with n=1 include bicyclo[2.2.1]hepta-2,5-diene.

(3) Examples of compounds with n=2 include bicyclo[2,2,2]octa-2,5-diene.

In the embodiment, the compound represented by the formula (a1) is preferably used, and n is more preferably 1. As the compound, specifically, a compound represented by the following formula (1) can be preferably used.

(1)

In the formula (1), X is the same as in the formula (a1), preferably a cyano group or an aldehyde group, and more preferably a cyano group.

Meanwhile, the compound represented by the formula (1) may be any one of an endo compound or an exo compound, or may be a mixture having endo and exo compounds at an arbitrary ratio.

The compound containing a metal belonging to Groups 8 to 10 which is used in the reaction of the embodiment is a rhodium compound, a cobalt compound, a ruthenium compound or an iron compound.

Examples of the rhodium compound include $Rh(acac)(CO)_2$, $Rh(aCaC)_3$, $RhCl(CO)(PPh_3)_2$, $RhCl(PPh_3)_3$, $RhBr(CO)(PPh_3)_2$, $Rh_2(CO)_8$, $Rh_4(CO)_{12}$, $Rh_6(CO)_{16}$ and the like. Examples of the cobalt compound include $HCo(CO)_3$, $HCo(CO)_4$, $Co_2(CO)_8$, $HCO_3(CO)_9$ and the like. Examples of the ruthenium compound include $Ru(CO)_3(PPh_3)_2$, $RuCl_2(PPh_3)_3$, $RuCl_3(PPh_3)_3$, $Ru_3(CO)_{12}$ and the like. In addition, examples of the iron compound include $Fe(CO)_5$, $Fe(CO)_4PPh_3$, $Fe(CO)_4(PPh_3)_2$ and the like. Meanwhile, "acac" refers to acetylacetonate.

The rhodium compound used in the reaction of the embodiment is not particularly limited as long as the rhodium compound includes monovalent rhodium metal, and examples thereof include rhodium carbonyl catalysts such as dicarbonyl acetylacetonate rhodium ($Rh(acac)(CO)_2$), dodecacarbonyl tetrarhodium ($Rh_4(CO)_{12}$), hexadecacarboncyl hexarhodium ($Rh_6(CO)_{16}$) and octacarbonyl dirhodium ($Rh_2(CO)_8$); rhodium chloride and the like.

The phosphorous compound used in the reaction of the embodiment is not particularly limited as long as the phosphorous compound is a trivalent phosphorous compound, and a compound represented by the following formula is preferably used.

In the formulae, $R^1$ and $R^2$ may be the same or different, and respectively represent alkyl groups having 1 to 16 carbon atoms or aryl groups having 6 to 16 carbon atoms which may have a substitute.

Specific examples of the phosphorous compound include trivalent phosphorous compounds such as triphenyl phosphite, triphenyl phosphine, trimethyl phosphine, triethyl phosphine, tripropyl phosphine, tri(methylbenzene)phosphine, tri(ethylbenzene)phosphine, 1,2-bis(diphenylphosphino)ethylene, 1,3-bis(diphenylphosphino)propane, 2,2-bis(diphenylphosphino)-1,1-binaphthyl, trimethoxy phosphite, triethoxy phosphite, tripropoxy phosphite, triisopropoxy phosphite, trimethyl phenyl phosphite and tris(2,4-ditert-butylphenyl)phosphite.

A hydroformylation reaction in which the above raw materials and the like are used can be carried out so as to satisfy "a condition (1)" and "a condition (2) and/or a condition (3)" which will be described below. In the embodiment, it is preferable to satisfy two conditions of the condition (1) and the condition (2).

The condition (1) is that a content of a metal belonging to Groups 8 to 10 which is included in the compound containing a metal belonging to Groups 8 to 10 with respect to 1 mol of the compound represented by the formula (a1) or (a2) is 0.01 ppm mol to 300 ppm mol, more preferably 0.15 ppm mol to 100 ppm mol, more preferably 0.5 ppm mol to 100 ppm mol, and particularly preferably 1 ppm mol to 100 ppm mol.

The condition (2) is that a molar ratio of "the phosphorous compound (mol)" to "the metal (mol) belonging to Groups 8 to 10 which is included in the compound containing a metal belonging to Groups 8 to 10" is 100 or more, preferably 150 or more, and more preferably 200 or more. An upper limit is not particularly limited; however, from the viewpoint of the above effects, the upper limit is 1,000,000 or less, preferably 100,000 or less, more preferably 50,000 or less, and particularly preferably 10,000 or less. The lower limit value and the upper limit value can be arbitrarily combined.

The condition (3) is that a molar ratio of "the phosphorous compound (mol)" to "the compound (mol) represented by the formula (a1) or (a2)" is 0.003 to 0.05, preferably 0.003 to 0.03, and more preferably 0.003 to 0.02.

Meanwhile, the numeric ranges in the above (1) to (3) can be arbitrarily combined.

In a process that satisfies the above conditions, even in a case in which the amount of the metal belonging to Groups 8 to 10 is reduced, the productivity of an aldehyde compound is excellent, and an aldehyde compound can be obtained at a high yield. A reason for obtaining the above effect is assumed that the activity of the compound containing a metal belonging to Groups 8 to 10 improves beyond expectation by increasing the use amount of the phosphorous compound. In addition, it is also assumed that the compound represented by the formula (a1) or (a2) has a high stereoscopic or electronic influence.

The aldehyde compound can be synthesized, specifically, in the following manner.

First, a rhodium compound, a phosphorous compound and a compound represented by the formula (a1) or (a2) of the raw material are inserted into a container. The aldehyde can be synthesized, while supplying hydrogen and carbon monoxide gas to the container, at a temperature of 30° C. to 120° C. and a pressure of 0.1 MPa to 1.0 MPa for a reaction time of 1 hour to 8 hours. Meanwhile, the hydroformylation reaction can be carried out by appropriately selecting a one phase reaction system made up of only an oil phase or a two phase reaction system made up of a water layer and an oil layer.

Thereby, the compound represented by the formula (a1) or (a2) undergoes hydroformylation, thereby synthesizing an aldehyde compound.

Meanwhile, the hydroformylation reaction can also be carried out under solventless condition, or a substituted or unsubstituted aromatic compound, a substituted or unsubstituted aliphatic hydrocarbon compound or an alcohol can be used, and, for example, the hydroformylation reaction can also be carried out in a solvent such as toluene, benzene, hexane, octane, acetonitrile, benzonitrile, ortho-dichlorobenzene, ethanol, pentanol or octanol. The hydroformylation reaction in the embodiment is also excellent in terms of reactivity at a high concentration, and therefore it is possible to carryout the hydroformylation reaction under solventless condition. Thereby, since a step for distilling a solvent becomes unnecessary, steps become simple, also, a volume efficiency also improves, and a production efficiency is also excellent.

An aldehyde compound represented by the formula (b1) is synthesized from the compound of the formula (a1) using the process of the embodiment. An aldehyde compound represented by the formula (b2) is synthesized from the compound of the formula (a2).

In a case in which n is 1 or 2, and X is not a hydrogen atom, the compound represented by the formula (b1) or (b2) can be obtained in a form of any one of "a compound having a second position and a fifth position substituted by a predetermined group (hereinafter, 2,5 body)" and "a compound having a second position and a sixth position substituted by a predetermined group (hereinafter, 2,6 body)" or a mixture including the above compounds at an arbitrary ratio. In addition, the 2,5 body and the 2,6 body can be respectively obtained in a form of any one of an endo-endo body, an endo-exo body and au exo-exo body depending on a steric configuration of the substituents, or can also be obtained in a form of a mixture including at least two of the bodies at an arbitrary ratio.

Meanwhile, in a case in which n is 0, and X is not a hydrogen atom, the compound represented by the formula (b1) or (b2) can be obtained in a form of any one of a cis-type and a trans-type, or can also be obtained in a form of a mixture including both types at an arbitrary ratio.

In the formula (b1) or (b2), X and n are the same as in the formula (a1) or (a2).

In the embodiment, the compound represented by the formula (b1) is preferably obtained, and examples of the compound include compounds represented by the following formula (2).

In the formula (2), X is the same as in the formula (1).

Meanwhile, the aldehyde compound represented by the formula (2) can be obtained in a form of any one of "a compound in which a second position of bicyclo[2.2.1]heptane is substituted by a substituent X and a fifth position is substituted by an aldehyde group (hereinafter, 2,5 body)" and "a compound in which a second position is substituted by the substituent X and a sixth position is substituted by an aldehyde group (hereinafter, 2,6 body)" or a mixture including the above compounds at an arbitrary ratio. In addition, the 2,5 body and the 2,6 body can be respectively obtained in a form of any one of an endo-endo body, an endo-exo body and an exo-exo body depending on a steric configuration of the substituents, or can also be obtained in a form of a mixture including at least two of the bodies at an arbitrary ratio.

After the completion of the hydroformylation reaction, a predetermined purification step is carried out, and a target aldehyde compound can be obtained.

<Process for Producing Amine Compounds>

The process for producing amine compounds of the embodiment includes the following steps.

Step (a): the compound represented by the formula (a1) or (a2) is reacted with a hydrogen and a carbon monoxide in the presence of a compound containing a metal belonging to Groups 8 to 10 and a phosphorous compound.

Step (b): the aldehyde compound obtained in Step (a) is reacted with an ammonia, and reacted with a hydrogen in the presence of a catalyst.

The process for producing amine compounds of the embodiment includes the process for producing aldehyde compounds as Step (a). Therefore, in Step (a), since it is possible to reduce the amount of the metal belonging to Groups 8 to 10, and, furthermore, the productivity and yield of the aldehyde compound are excellent, the productivity and yield of an amine compound which is a target compound also become excellent.

Meanwhile, since Step (a) is the same as the step in the "process for producing aldehyde compounds", description thereof is not repeated.

In Step (b), the aldehyde compound represented by the formula (b1) or the formula (b2) which is obtained in Step (a) is reacted with an ammonia so as to produce an imino compound, and hydrogen is added in the presence of a catalyst, thereby synthesizing an amine compound.

A metal catalyst, such as nickel, platinum, palladium, ruthenium can be used as the catalyst. In a case in which the aldehyde compound includes a cyano group as a substituent, a —$CH_2$—$NH_2$ group is produced through hydrogen reduction.

As such, in Step (b), since an aldehyde group included in the aldehyde compound is changed to an amino group through iminorization, and a cyano group is also changed to an amino group through hydrogen reduction, an amine compound represented by the following formula (c1) which has two amino groups is synthesized. Meanwhile, in a case in which X is a hydrogen atom, an amine compound represented by the following formula (c2) is synthesized.

In the formula (c1) or (c2), n is the same as in the formula (a1) or (a2)

In a case in which n is 1 or 2, the compound represented by the formula (c1) can be obtained in a form of any one of "the compound having a second position and a fifth position substituted by a predetermined group (hereinafter, 2,5 body)"

and "the compound having a second position and a sixth position substituted by a predetermined group (hereinafter, 2,6 body)" or a mixture including the above compounds at an arbitrary ratio. In addition, the 2,5 body and the 2,6 body can be respectively obtained in a form of any one of an endo-endo body, an endo-exo body and an exo-exo body depending on a steric configuration of the substituents, or can also be obtained in a form of a mixture including at least two of the bodies at an arbitrary ratio.

Meanwhile, in a case in which n is 0, the compound represented by the formula (c1) can be obtained in a form of any one of a cis-type and a trans-type, or can also be obtained in a form of a mixture including both types at an arbitrary ratio.

In a case in which n is 1 or 2, the compound represented by the formula (c2) can be obtained in a form of an endo body or an exo body, and can also be obtained in a form of a mixture including both bodies at an arbitrary ratio.

The compound of the formula (c1) is preferably obtained, and examples of the compound include compounds of the following chemical formula (3) for which n is 1.

(3)

Meanwhile, the amine compound represented by the chemical formula (3) can be obtained in a form of any one of "a compound in which a second position and a fifth position of bicyclo[2.2.1]heptane are substituted by an aminomethyl group (hereinafter, 2,5 body)" and "a compound in which a second position and a sixth position are substituted by an aminomethyl group (hereinafter, 2,6 body)" or a mixture including the above compounds at an arbitrary ratio. In addition, the 2,5 body and the 2,6 body can be respectively obtained in a form of any one of an endo-endo body, an endo-exo body and an exo-exo body depending on a steric configuration of the substituents, or can also be obtained in a form of a mixture including at least two of the bodies at an arbitrary ratio.

The amination and the hydrogen addition reaction can be carried out, specifically, in the following manner. First, an aldehyde compound, a solvent and a catalyst are prepared in a reaction container, and ammonia gas is blown in it. Then, hydrogen is injected until a pressure of approximately 1 MPa, the temperature is increased to approximately 100° C., and the components are reacted at the above temperature and the above pressure for approximately 1 to 10 hours while supplying hydrogen. As the solvent, for example, an alcohol having 1 to 8 carbon atoms, water or the like is preferably used.

Furthermore, after the completion of the reaction, ordinary catalytic filtration, desolvation, a purification step and the like are carried out to obtain a target amine compound.

<Process for Producing Isocyanate Compounds>

The process for producing isocyanate compounds of the embodiment includes the following steps.

Step (a): the compound represented by the formula (a1) or (a2) is reacted with a hydrogen and a carbon monoxide in the presence of a compound containing a metal belonging to Groups 8 to 10 and a phosphorous compound.

Step (b): the aldehyde compound obtained in Step (a) is reacted with an ammonia, and reacted with a hydrogen in the presence of a catalyst.

Step (c): the amine compound obtained in Step (b) is reacted with a carbonylating agent.

The process for producing isocyanate compounds of the embodiment includes the process for producing aldehyde compounds as Step (a). Therefore, in Step (a), since it is possible to reduce the amount of the compound containing a metal belonging to Groups 8 to 10, and, furthermore, the productivity and yield of the aldehyde compound are excellent, the productivity and yield of an isocyanate compound which is a target compound also become excellent.

Meanwhile, since Step (a) is the same as the step in the "process for producing aldehyde compounds", and Step (b) is the same as the step in the "process for producing amine compounds", description thereof will not be repeated.

In Step (c), the amine compound represented by the formula (c1) or the formula (c2) which is obtained in Step (b) is reacted with a carbonylating agent under predetermined conditions to synthesize an isocyanate compound represented by the formula (d1) or (d2). As the carbonylating agent, phosgene, a urea derivative, a carbonate derivative, monoxide carbon and the like can be used.

In the formula (d1) or (d2), n is the same as in the formula (a1) or (a2).

In a case in which n is 1 or 2, the compound represented by the formula (d1) can be obtained in a form of any one of "a compound having a second position and a fifth position substituted by a predetermined group (hereinafter, 2,5 body)" and "a compound having a second position and a sixth position substituted by a predetermined group (hereinafter, 2,6 body)" or a mixture including the above compounds at an arbitrary ratio. In addition, the 2,5 body and the 2,6 body can be respectively obtained in a form of any one of an endo-endo body, an endo-exo body and an exo-exo body depending on a steric configuration of the substituents, or can also be obtained in a form of a mixture including at least two of the bodies at an arbitrary ratio.

Meanwhile, in a case in which n is 0, the compound represented by the formula (d1) can be obtained in a form of any one of a cis-type and a trans-type, or can also be obtained in a form of a mixture including both types at an arbitrary ratio.

In a case in which n is 1 or 2, the compound represented by the formula (d2) can be obtained in a form of an endo body or an exo body, and can also be obtained in a form of a mixture including both bodies at an arbitrary ratio.

The compound of the formula (d1) is preferably obtained, and examples of the compound include compounds of the following formula (4) for which n is 1.

(4)

Meanwhile, the isocyanate compound represented by the formula (4) can be obtained in a form of any one of "a compound in which a second position and a fifth position of bicyclo[2.2.1]heptane are substituted by an isocyanate methyl group (hereinafter, 2,5 body)" and "a compound in which a second position and a sixth position are substituted by an isocyanate methyl group (hereinafter, 2,6 body)" or a mixture including the above compounds at an arbitrary ratio. In addition, the 2,5 body and the 2,6 body can be respectively obtained in a form of any one of an endo-endo body, an endo-exo body and an exo-exo body depending on a steric configuration of the substituents, or can also be obtained in a form of a mixture including at least two of the bodies at an arbitrary ratio.

In a case in which phosgene is used as the carbonylating agent, examples of Step (c) include a process in which, specifically, first, an amine compound is added into a reaction container with a solvent, changed to hydrochloride using hydrochloric acid, and then reacted with phosgene, a process in which an amine compound is directly reacted with phosgene so as to obtain a carbamoyl chloride compound, and then the compound is thermally decomposed, and the like. Furthermore, after the completion of the reaction, an ordinary purification step and the like are carried out, and a target isocyanate compound can be obtained.

Meanwhile, the reaction solvent in a case in which phosgene is used as the carbonylating agent is not particularly limited, but a high-boiling-point organic aromatic compound or an ester compound which has a large solubility of hydrochloric acid during a salt-producing reaction, a large solubility of phosgene and a small solubility of hydrochloric acid during a phosgene reaction. Examples of the high-boiling-point organic aromatic compound include 1,2-diethylbenzene, 1,3-diethylbenzene, 1,4-diethylbenzene, isopropylbenzene, 1,2,4-trimethylbenzene, amylbenzene, diamylbenzene, triamylbenzene, dodecylbenzene, p-cymene, cumene methylphenyl ether, ethylphenyl ether, diisoamyl ether, n-hexyl ether, ortho-dichlorobenzene, para-chlorotoluene, bromobenzene, 1,2,4-trichlorobenzene and the like. In addition, the ester compound is not particularly limited, but is preferably acetate ester such as isoamyl acetate or isooctyl acetate. Among the above exemplified solvents, a particularly preferable solvent for carrying out the invention is an aromatic halogen compound.

The isocyanate compound obtained using the embodiment can be used as a raw material of optical materials or a coating material. Meanwhile, the amine compound obtained using the embodiment can also be used as coating materials and a raw material of curing agents.

EXAMPLES

Hereinafter, the invention will be described more specifically using examples and the like, but the scope of the invention is not limited to the examples and the like.

Reference Example

Synthesis of bicyclo[2.2.1]-5-heptene-2-carbonitrile

Acrylonitrile (163.6 g, 3.08 mol) to which dicyclopentadiene having a purity of 95% (195.0 g, 1.40 mol) and N-nitrosodiphenylamine (0.36 g, 1.8 mmol) were added was added into a 1000 ml autoclave, reacted under stirring at 160° C. for 5 hours, then, further heated, and reacted at 180° C. for 2 hours. A reaction liquid including an obtained bicyclo[2.2.1]-5-heptene-2-carbonitrile weighed 355.6 g, and an analysis showed that 331.2 g (2.78 mol) of bicyclo[2.2.1]-5-heptene-2-carbonitrile was included. 352.4 g of the reaction liquid including 328.2 g (2.75 mol) of the obtained bicyclo[2.2.1]-5-heptene-2-carbonitrile was added into a 500 ml flask, and distilled under reduced pressure, thereby obtaining bicyclo[2.2.1]-5-heptene-2-carbonitrile (300.7 g, 2.52 mol) as a principle distillate.

Example 1

Synthesis of 2-cyano-5-formyl bicyclo[2.2.1]heptane and 2-cyano-6-formyl bicyclo[2.2.1]heptane Rhodium acetylacetonate dicarbonyl (3.7 mg, 0.014 mmol), bicyclo[2.2.1]-5-heptene-2-carbonitrile (168.73 g, 1.4 mol) obtained in Reference Example, triphenyl phosphite (4.45 g, 14.3 mmol), toluene (59.0 g) were added into an SUS316L autoclave of electromagnetic stirring having an inner volume of 0.5 liter, and stirred at 25° C., thereby obtaining an Rh catalyst adjustment liquid (232.2 g). Meanwhile, Conditions (1) to (3) were as follows.

Use amount of rhodium (Condition (1)): an amount of rhodium included in rhodium acetylacetonate dicarbonyl was 10 ppm mol with respect to 1 mol of bicyclo[2.2.1]-5-heptene-2-carbonitrile.

Content of a phosphorous compound (a) (Condition (2)): triphenyl phosphite (mol)/rhodium (mol) included in rhodium acetylacetonate dicarbonyl: 1000

Content of a phosphorous compound (b) (Condition (3)): triphenyl phosphite (mol)/bicyclo[2.2.1]-5-heptene-2-carbonitrile (mol): 0.01

Next, the inside of the autoclave was sufficiently substituted by nitrogen, and then sufficiently substituted by a gas mixture having a volume ratio of carbon monoxide to hydrogen of 50/50. The same gas was injected until a pressure in the autoclave reached 0.6 MPaG, and the adjustment liquid was heated to 100° C. under stirring, thereby initiating a hydroformylation reaction. Since the pressure in the autoclave decreased with proceeds of the reaction, the gas mixture was continuously supplied so that the pressure was maintained at 0.6 MPaG, the temperature was adjusted so as to be maintained at 100° C., and the reaction was carried out for 6 hours. After the completion of the reaction, the gas mixture in the system was purged using nitrogen, and a reaction liquid including 2-cyano-5, (6)-formyl bicyclo[2.2.1]heptane (241.0 g) was obtained. An analysis showed that the reaction liquid contained 208.8 g (1.4 mol) of 2-cyano-5-formyl bicyclo[2.2.1]heptane and 2-cyano-6-formyl bicyclo[2.2.1]heptane.

2-cyano-5,(6)-formyl bicyclo[2.2.1]heptane (255.1 g, 1.71 mol), 263.8 g of a reaction liquid including of triphenyl phosphate (4.7 g (0.02 mol)) and water (14.0 g) were added into a four-neck reaction flask which was equipped with a reflux cooling tube, stirring blades and a thermometer, and had an inner volume of 2 liter, stirred, heated to 80° C., and hydrolyzed over 2 hours. An analysis showed that the obtained solution contained 252.1 g (1.69 mol) of 2-cyano-5-formyl bicyclo[2.2.1]heptane and 2-cyano-6-formyl bicyclo[2.2.1] heptane, and triphenyl phosphite was not detected.

6.4 g of 20 weight % aqueous solution of potassium hydrogen carbonate (0.012 mol) was added dropwise to a hydrolysis solution at 25° C. until pH was reached at 7.0.

Figure 1:
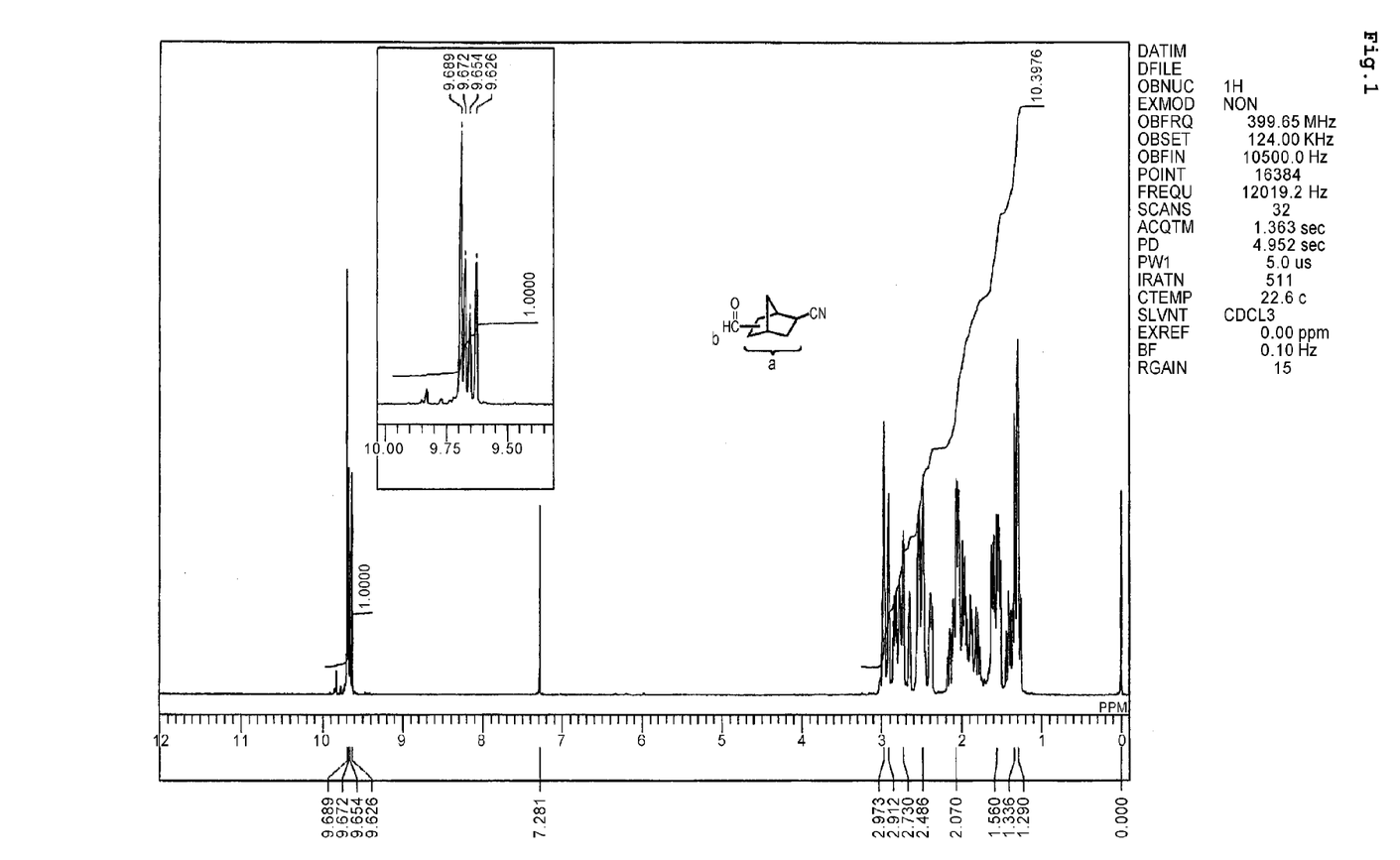
FIG. 1 is an $^1$H-NMR chart of a compound obtained in Example 1.

Next, distillation was carried out under reduced pressure, and a solution (264 g) including 250.6 g (1.68 mol) of 2-cyano-5-formyl bicyclo[2.2.1]heptane and 2-cyano-6-formyl bicyclo[2.2.1]heptane was obtained. The solution was distilled and purified under reduced pressure, and a mixture (244.7 g, 1.64 mol) of 2-cyano-5-formyl bicyclo[2.2.1]heptane and 2-cyano-6-formyl bicyclo[2.2.1]heptane was obtained. An $^1$H-NMR chart is illustrated in FIG. 1.

Example 2

Synthesis of
2,5-bisaminomethyl-bicyclo[2.2.1]heptane and
2,6-bisaminomethyl-bicyclo[2.2.1]heptane 89.5 g (0.6 mol) of 2-Cyano-5-formyl bicyclo[2.2.1]heptane and 2-cyano-6-formyl bicyclo[2.2.1]heptane which had been obtained in Example 1, methanol (89.5 g) and 4.5 g (as dried mass) of Raney cobalt catalyst (cobalt 94 mass %, aluminum 3.5 mass %, manganese 2.1 mass %) obtained by developing a cobalt-aluminum alloy containing manganese were added in a stainless steel autoclave of electromagnetic stirring having an inner volume of 0.5 liter, and ammonia gas (24.5 g, 1.44 mol) was blown in the autoclave.

Next, the inside of the autoclave was sufficiently substituted by nitrogen, and then continuously substituted by hydrogen. In addition, hydrogen was injected until a pressure in the autoclave reached 1.2 MPaG, and a solution was heated to 100° C. under stirring, thereby initiating a reaction. Since the pressure in the autoclave decreased with proceeds of the reaction, hydrogen was continuously supplied so that the pressure was maintained at 1.2 MPaG, the temperature was adjusted so as to be maintained at 100° C., and a hydrogenation reaction was carried out for 6 hours.

The solution was cooled to room temperature, the Raney cobalt catalyst was removed through filtration, and then ammonia and methanol were distilled at 4 kPa and 60° C., thereby obtaining a solution (102.0 g) including 2,5-bisaminomethyl-bicyclo[2.2.1]heptane and 2,6-bisaminomethyl-bicyclo[2.2.1]heptane.

Figure 2:
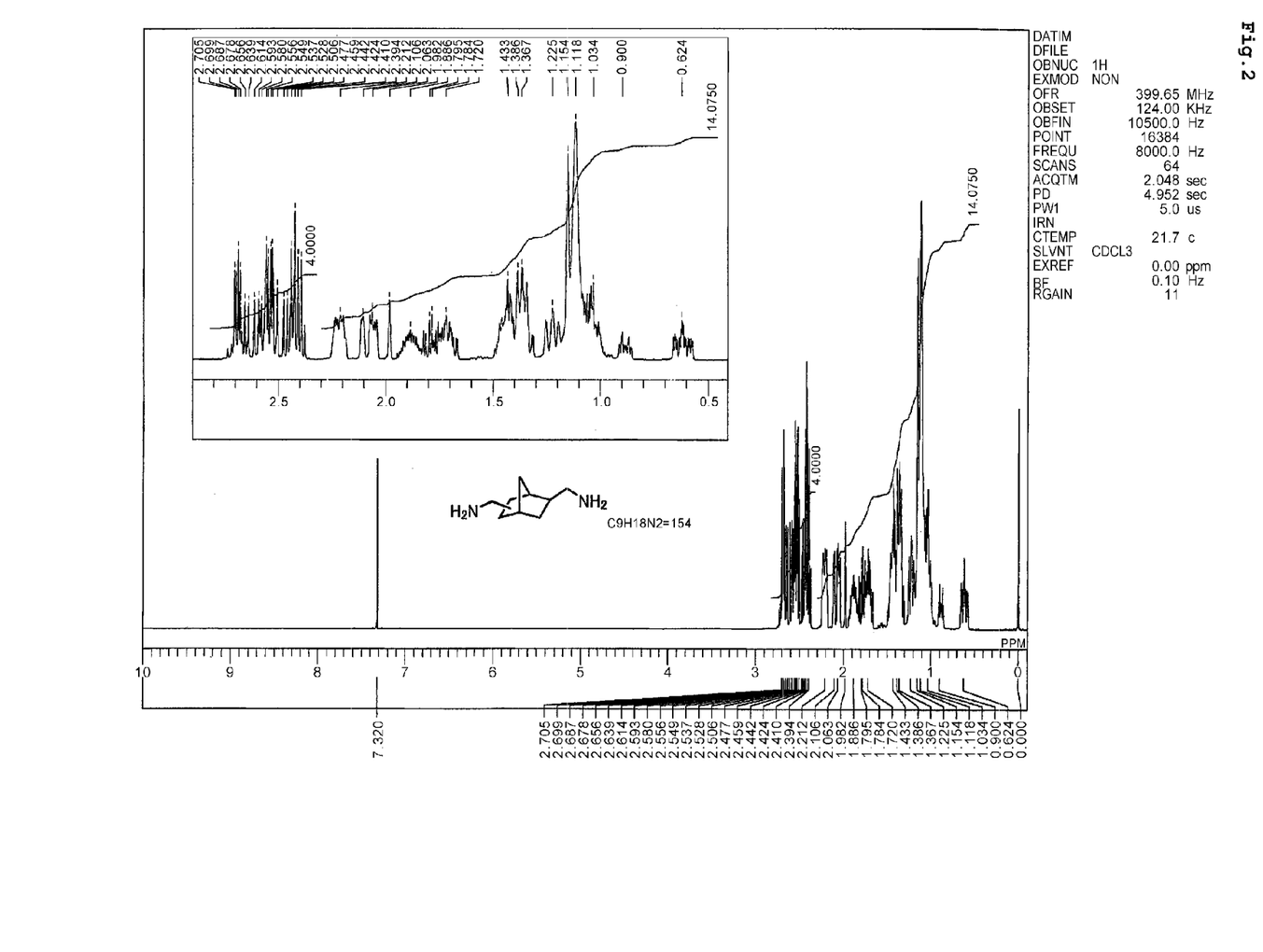
FIG. 2 is an $^1$H-NMR chart of a compound obtained in Example 2.

The obtained solution (102.0 g) including 2,5-bisaminomethyl-bicyclo[2.2.1]heptane and 2,6-bisaminomethyl-bicyclo[2.2.1]heptane was added into a 200 ml flask, and distilled under reduced pressure, thereby obtaining a mixture (79.0 g) of the purified 2,5-bisaminomethyl-bicyclo[2.2.1]heptane and 2,6-bisaminomethyl-bicyclo[2.2.1]heptane. An $^1$H-NMR chart is illustrated in FIG. 2.

Example 3

Figure 3:
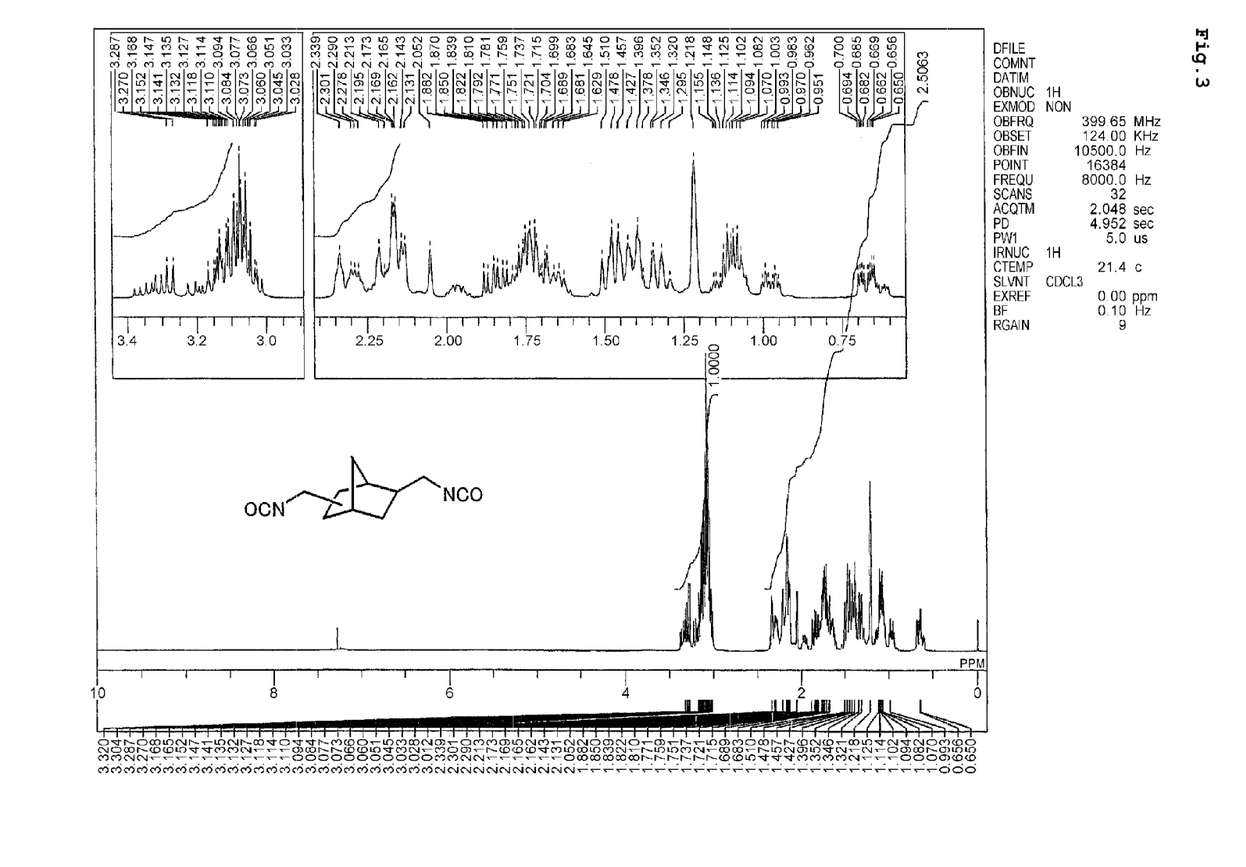
FIG. 3 is an $^1$H-NMR chart of a compound obtained in Example 3.

Synthesis of 2,5-bisisocyanate
methyl-bicyclo[2.2.1]heptane and 2,6-bisisocyanate
methyl-bicyclo[2.2.1]heptane Ortho-dichlorobenzene (958 g) was added into a five-neck flask which is equipped with a reflux cooling tube, stirring blades, a thermometer, a gas-blowing tube and a raw material-injecting tube, and had an inner volume of 2 liter, 154.2 g (1.0 mol) of 2,5-bisaminomethyl-bicyclo[2.2.1]heptane and 2,6-bisaminomethyl-bicyclo[2.2.1]heptane which had been obtained in Example 2 and ortho-dichlorobenzene (702 g) were prepared in a raw material tank. Next, a reaction container was heated to 120° C. at 0.1 MPa, adding of hydrochloric acid gas from a hydrochloric acid-blowing tube at a rate of 43.8 g/hr and adding of an amine diluted by a solvent from the raw material tank using a raw material-injecting pump at a rate of 428.1 g/hr were initiated at the same time, and the total amount was added over 2 hours. Furthermore, aging was carried out for 1 hour while adding hydrochloric acid gas at 20 g/hr. After the completion of the reaction, subsequently, hydrochloride reaction mass was heated to 160° C., phosgene was blown in from a phosgene-blowing tube at 100 g/hr (1.0 mol/hr), and a reaction was caused for 6 hours while maintaining the temperature. After the completion of the reaction, unreacted phosgene and hydrochloric acid gas in the system were purged using nitrogen, and the solvent was removed, thereby obtaining a solution (200.9 g) including 2,5-bisisocyanate methyl-bicyclo[2.2.1]heptane and 2,6-bisisocyanate methyl-bicyclo[2.2.1]heptane. Furthermore, distillation was carried out under reduced pressure, and a mixture (175.7 g) of 2,5-bisisocyanate methyl-bicyclo[2.2.1]heptane and 2,6-bisisocyanate methyl-bicyclo[2.2.1]heptane having a purity of 99.0% was obtained. An $^1$H-NMR chart is illustrated in FIG. 3.

Example 4

Synthesis of 2-cyano-5-formyl bicyclo[2.2.1]heptane
and 2-cyano-6-formyl bicyclo[2.2.1]heptane Rhodium acetylacetonate dicarbonyl (4.64 mg, 0.018 mmol), bicyclo[2.2.1]-5-heptene-2-carbonitrile (215.3 g, 1.8 mol) obtained in Reference Example and triphenyl phosphite (5.59 g, 18.0 mmol) were stirred at 25° C. in an SUS316L autoclave of electromagnetic stirring having an inner volume of 0.5 liter, thereby obtaining an Rh catalyst adjustment liquid (220.9 g). Meanwhile, Conditions (1) to (3) were as follows.

Use amount of rhodium (Condition (1)): an amount of rhodium included in rhodium acetylacetonate dicarbonyl was 10 ppm mol with respect to 1 mol of bicyclo[2.2.1]-5-heptene-2-carbonitrile.

Content of a phosphorous compound (a) (Condition (2)): triphenyl phosphite (mol)/rhodium (mol) included in rhodium acetylacetate dicarbonyl: 1000

Content of a phosphorous compound (b) (Condition (3)): triphenyl phosphite (mol)/bicyclo[2.2.1]-5-heptene-2-carbonitrile (mol): 0.01

Next, the inside of the autoclave was sufficiently substituted by nitrogen, and then sufficiently substituted by a gas mixture having a volume ratio of carbon monoxide to hydrogen of 50/50. The same gas was injected until a pressure in the autoclave reached 0.6 MPaG, and the adjustment liquid was heated to 100° C. under stirring, thereby initiating a hydroformylation reaction. Since the pressure in the autoclave decreased with proceeds of the reaction, the gas mixture was continuously supplied so that the pressure was maintained at 0.6 MPaG, the temperature was adjusted so as to be maintained at 100° C., and the hydroformylation reaction was carried out for 6 hours. After the completion of the reaction, the gas mixture in the system was purged using nitrogen, and 276.7 g of a reaction liquid including 2-cyano-5-formyl bicyclo[2.2.1]heptane and 2-cyano-6-formyl bicyclo[2.2.1]heptane was obtained. An analysis showed that the reaction liquid contained 261.8 g (1.76 mol) of the compounds.

Example 5

"A mixture of 2,5-bisaminomethyl-bicyclo[2.2.1]heptane and 2,6-bisaminomethyl-bicyclo[2.2.1]heptane" was synthesized from "the mixture of 2-cyano-5-formyl bicyclo[2.2.1]heptane and 2-cyano-6-formyl bicyclo[2.2.1]heptane" obtained in Example 4 according to Example 2. The yield was 85.6%.

Example 6

"A mixture of 2,5-bisisocyanate methyl-bicyclo[2.2.1]heptane and 2,6-bisisocyanate methyl-bicyclo[2.2.1]heptane" was synthesized from "the mixture of 2,5-bisaminomethyl-bicyclo[2.2.1]heptane and 2,6-bisaminomethyl-bicyclo[2.2.1]heptane" obtained in Example 5 according to Example 3. The yield after distillation was 85.6%.

Examples 7 to 21, Comparative Examples 1 to 3

Aldehyde compounds were synthesized according to the process of Example 1 in a case in which a solvent was used and according to the process of Example 3 in a case in which a solvent was not used so that amounts and reaction pressures described in Table 1 were reached. The results are described in Table 1.

Example 22

Synthesis of 2,5-bisformyl bicyclo[2.2.1]heptane and 2,6-bisformyl bicyclo[2.2.1]heptane Rhodium acetylacetonate dicarbonyl (4.64 mg, 0.018 mmol), bicyclo[2.2.1]-5-heptene-2-carboxyaldehyde (219.9 g, 1.8 mol) and triphenyl phosphite (5.59 g, 18.0 mmol) were stirred at 25° C. in an SUS316L autoclave of electromagnetic stirring having an inner volume of 0.5 liter, thereby obtaining an Rh catalyst adjustment liquid (225.5 g). Meanwhile, Conditions (1) to (3) were as follows.

Use amount of rhodium (Condition (1)): an amount of rhodium included in rhodium acetylacetonate dicarbonyl was 10 ppm mol with respect to 1 mol of bicyclo[2.2.1]-5-heptene-2-carboxyaldehyde.

Content of a phosphorous compound (a) (Condition (2)): triphenyl phosphite (mol)/rhodium (mol) included in rhodium acetylacetonate dicarbonyl: 1000

Content of a phosphorous compound (b) (Condition (3)): triphenyl phosphite (mol)/bicyclo[2.2.1]-5-heptene-2-carboxyaldehyde (mol): 0.01

Next, the inside of the autoclave was sufficiently substituted by nitrogen, and then sufficiently substituted by a gas mixture having a volume ratio of carbon monoxide to hydrogen of 50/50. The same gas was injected until a pressure in the autoclave reached 0.6 MPaG, and the adjustment liquid was heated to 100° C. under stirring, thereby initiating a hydroformylation reaction. Since the pressure in the autoclave decreased with proceeds of the reaction, the gas mixture was continuously supplied so that the pressure was maintained at 0.6 MPaG, the temperature was adjusted so as to be maintained at 100° C., and the hydroformylation reaction was carried out for 6 hours. After the completion of the reaction, the gas mixture in the system was purged using nitrogen, and 280.1 g of a reaction liquid including 2,5-bisformyl bicyclo[2.2.1]heptane and 2,6-bisformyl bicyclo[2.2.1]heptane was obtained. An analysis showed that the reaction liquid contained 266.1 g (1.76 mol) of the compounds.

Meanwhile, the Examples describe that the mixture of the compound in which a second position and a fifth position of bicyclo[2.2.1]heptane were substituted (2,5 body) and the compound in which a second position and a sixth position were substituted (2,6 body) was obtained as an example, but any one of the 2,5 body and the 2,6 body can be obtained depending on reaction conditions. In addition, the 2,5 body can be obtained in a form of any one of an endo-endo body, an endo-exo body and an exo-exo body depending on a steric configuration of the substituents, or can also be obtained in a form of a mixture including at least two of the bodies at an arbitrary ratio. Similarly, the 2,6 body can be obtained in a form of any one of an endo-endo body, an endo-exo body and an oxo-exo body, or can also be obtained in a form of a mixture including at least two of the bodies at an arbitrary ratio.

TABLE 1

| No. | | Use amount of rhodium ppmmol/raw material | Content of phosphorous compound (a) mol/Rh (mol) | Content of phosphorous compound (b) mol/raw material (mol) | Yield mol %/raw material | Toluene solvent | Reaction pressure MPa |
|---|---|---|---|---|---|---|---|
| Example | 1 | 10 | 1000 | 0.010 | 100.0 | Yes | 0.6 |
|  | 4 | 10 | 1000 | 0.010 | 96.7 | No |  |
|  | 7 | 100 | 187 | 0.019 | 100.0 | Yes |  |
|  | 8 | 38 | 264 | 0.010 | 98.2 | Yes |  |
|  | 9 | 20 | 506 | 0.010 | 98.3 | Yes |  |
|  | 10 | 10 | 800 | 0.008 | 98.4 | Yes |  |
|  | 11 | 10 | 1200 | 0.012 | 100.0 | Yes |  |
|  | 12 | 5 | 1500 | 0.008 | 100.0 | No |  |
|  | 13 | 5 | 2000 | 0.010 | 100.0 | No |  |
|  | 14 | 5 | 2000 | 0.010 | 98.0 | Yes |  |
|  | 15 | 2.5 | 2000 | 0.005 | 97.1 | No |  |
|  | 16 | 2.5 | 4000 | 0.010 | 100.0 | No |  |
|  | 17 | 1 | 10000 | 0.010 | 100.0 | Yes |  |
|  | 18 | 5 | 1000 | 0.005 | 92.1 | No |  |
|  | 19 | 5 | 500 | 0.003 | 88.4 | No |  |
|  | 20 | 5 | 2000 | 0.010 | 97.5 | No | 0.3 |
|  | 21 | 0.12 | 10155 | 0.001 | 38.6 | No | 0.6 |
|  | 22 | 10 | 2000 | 0.020 | 60.0 | Yes | 0.6 |
| Comparative Example | 1 | 1160 | 16 | 0.019 | 99.5 | Yes | 0.6 |
|  | 2 | 100 | 16 | 0.002 | 82.5 | Yes |  |
|  | 3 | 20 | 16 | 0.00008 | 0 | Yes |  |

The present application claims priority based on Japanese Patent Application No. 2011-104401 filed on May 9, 2011, the contents of which are incorporated herein for reference.

The invention includes the following contents.

[a] A process for producing aldehyde compounds comprising:
reacting a compound represented by the following formula (1) with a hydrogen and a carbon monoxide in the presence of a rhodium compound and a phosphorous compound so as to satisfy the following conditions (1) and (2);
wherein the condition (1) is that a content of rhodium included in the rhodium compound is 0.01 ppm mol to 300 ppm mol with respect to 1 mol of the compound represented by the formula (1), and wherein the condition (2) is that a molar ratio represented by the phosphorous compound (mol)/the rhodium (mol) is 100 or more, (1)

wherein, in the formula (1), X represents a cyano group or an aldehyde group.

[b] The process for producing aldehyde compounds described in [a], the phosphorous compound is a trivalent phosphorous compound.

[c] The process for producing aldehyde compounds described in [a] or [b], the reacting step is carried out under solventless condition.

[d] A process for producing amine compounds comprising:
reacting an aldehyde compound obtained using the process described in any one of [a] to [c] with an ammonia, and reacting with a hydrogen in the presence of a catalyst.

[e] A process for producing isocyanate compounds comprising:
reacting an amine compound obtained using the process described in [d] with a carbonylating agent.

[f] A process for producing amine compounds comprising:
reacting a compound represented by the following formula (1) with a hydrogen and a carbon monoxide in the presence of a rhodium compound and a phosphorous compound so as to satisfy the following conditions (1) and (2), and
reacting the aldehyde compound with an ammonia, and reacting with a hydrogen in the presence of a catalyst;
wherein the condition (1) is that a content of rhodium included in the rhodium compound is 0.01 ppm mol to 300 mol with respect to 1 mol of the compound represented by the formula (1), and
wherein the condition (2) is that a molar ratio represented by the phosphorous compound (mol)/the rhodium (mol) is 100 or more, (1)

wherein, in the formula (1), X represents a cyano group or an aldehyde group.

[g] A process for producing isocyanate compounds comprising:
reacting a compound represented by the following formula (1) with a hydrogen and a carbon monoxide in the presence of a rhodium compound and a phosphorous compound so as to satisfy the following conditions (1) and (2), thereby synthesizing an aldehyde compound,
reacting the aldehyde compound with an ammonia, and reacting with a hydrogen in the presence of a catalyst, and
reacting the amine compound with a carbonylating agent;
wherein the condition (1) is that a content of rhodium included in the rhodium compound is 0.01 ppm mol to 300 ppm mol with respect to 1 mol of the compound represented by the formula (1), and wherein the condition (2) is that a molar ratio represented by the phosphorous compound (mol)/the rhodium (mol) is 100 or more, (1)

wherein, in the formula (1), X represents a cyano group or an aldehyde group.

The invention claimed is:
1. A process for producing an aldehyde compound represented by the following formula (b1) or the following formula (b2) comprising:
a step of reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2);
wherein the condition (1) is that a content of a metal included in the compound containing a metal belonging to Groups 8 to 10 is 0.015 ppm mol to 100 ppm mol with respect to 1 mol of the compound represented by the following formula (a1) or (a2), and
wherein the condition (2) is that a molar ratio represented by the phosphorous compound (mol)/the metal (mol) is 150 or more, wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2, wherein n and X are previously described, and
wherein the reacting step further satisfies the condition (3) in which is that a molar ratio of "the phosphorous compound (mol)" to "the compound (mol) represented by the formula (a1) or (a2)" is 0.003 to 0.05.

2. The process for producing the aldehyde compound according to claim 1,
wherein the compound containing a metal belonging to Groups 8 to 10 is a rhodium compound, a cobalt compound, a ruthenium compound or an iron compound.

3. The process for producing the aldehyde compound according to claim 1,
wherein the compound containing a metal belonging to Groups 8 to 10 is a rhodium compound.

4. The process for producing the aldehyde compound according to claim 1,
wherein the compound represented by the formula (a1) is used, and the compound is represented by the following formula (1)

(1)

wherein, in the formula (1), X is the same as in the formula (a1).

5. The process for producing the aldehyde compound according to claim 1,
wherein the phosphorous compound is a trivalent phosphorous compound.

6. The process for producing the aldehyde compound according to claim 5,
wherein the trivalent phosphorous compound is selected from group consisting of triphenyl phosphite, triphenyl phosphine, trimethyl phosphine, triethyl phosphine, tripropyl phosphine, tri(methylbenzene)phosphine, tri(ethylbenzene)phosphine, 1,2-bis(diphenylphosphino) ethylene, 1,3-bis(diphenylphosphino)propane, 2,2-bis(diphenylphosphino)-1,1-binaphthyl, trimethoxy phosphite, triethoxy phosphite, tripropoxy phosphite, triisopropoxy phosphite, trimethyl phenyl phosphite and tris(2,4-ditert-butylphenyl)phosphite.

7. The process for producing the aldehyde compound according to claim 1,
wherein the reacting step is carried out under solventless condition.

8. A process for producing an amine compound represented by the following formula (c1) or the following formula (c2) comprising:
a step (a) of reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2) to synthesize an aldehyde compound represented by the following formula (b1) or the following formula (b2); and
a step (b) of reacting the aldehyde compound with an ammonia, and reacting with a hydrogen in a presence of a catalyst;
wherein the condition (1) is that a content of a metal included in the compound containing a metal belonging to Groups 8 to 10 is 0.015 ppm mol to 100 ppm mol with respect to 1 mol of the compound represented by the following formula (a1) or (a2), and
wherein the condition (2) is that a molar ratio represented by the phosphorous compound (mol)/the metal (mol) is 150 or more, (a1)

(a2)

wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2, (b1)

(b2)

wherein n and X are previously described, (c1)

(c2)

wherein n is previously described, and
wherein the step (a) further satisfies the condition (3) in which is that a molar ratio of "the phosphorous compound (mol)" to "the compound (mol) represented by the formula (a1) or (a2)" is 0.003 to 0.05.

9. The process for producing the amine compound according to claim 8,
wherein the compound containing a metal belonging to Groups 8 to 10 is a rhodium compound, a cobalt compound, a ruthenium compound or an iron compound.

10. The process for producing the amine compound according to claim 8,
wherein the compound containing a metal belonging to Groups 8 to 10 is a rhodium compound.

11. The process for producing the amine compound according to claim 8,
wherein the compound represented by the formula (a1) is used, and that compound is represented by the following formula (1);

(1)

wherein, in the formula (1), X is the same as in the formula (a1).

12. The process for producing the isocyanate compound according to claim 11, wherein the phosphorous compound is selected from group consisting of triphenyl phosphite, triphenyl phosphine, trimethyl phosphine, triethyl phosphine, tripropyl phosphine, tri(methylbenzene)phosphine, tri(ethylbenzene) phosphine, 1,2-bis(diphenylphosphino)ethylene, 1,3-bis(diphenylphosphino)propane, 2,2-bis(diphenylphosphino)-1,1-binaphthyl, trimethoxy phosphite, triethoxy phosphite, tripropoxy phosphite, triisopropoxy phosphite, trimethyl phenyl phosphite and tris(2,4-ditert-butylphenyl)phosphite.

13. The process for producing the amine compound according to claim 8, wherein the trivalent phosphorous compound is selected from group consisting of triphenyl phosphite, triphenyl phosphine, trimethyl phosphine, triethyl phosphine, tripropyl phosphine, tri(methylbenzene)phosphine, tri(ethylbenzene)phosphine, 1,2-bis(diphenylphosphino)ethylene, 1,3-bis(diphenylphosphino)propane, 2,2-bis(diphenylphosphino)-1,1-binaphthyl, trimethoxy phosphite, triethoxy phosphite, tripropoxy phosphite, triisopropoxy phosphite, trimethyl phenyl phosphite and tris(2,4-ditert-butylphenyl)phosphite.

14. A process for producing an isocyanate compound represented by the following formula (d1) or the following formula (d2) comprising:

a step (a) of reacting a compound represented by the following formula (a1) or the following formula (a2) with a hydrogen and a carbon monoxide in a presence of a compound containing a metal belonging to Groups 8 to 10 and a phosphorous compound so as to satisfy the following conditions (1) and (2) to synthesize an aldehyde compound represented by the following formula (b1) or the following formula (b2);

a step (b) of reacting the aldehyde compound with an ammonia, and reacting with a hydrogen in a presence of a catalyst to synthesize an amine compound represented by the following formula (c1) or the following formula (c2); and a step (c) of reacting the amine compound with a carbonylating agent;

wherein the condition (1) is that a content of a metal included in the compound containing a metal belonging to Groups 8 to 10 is 0.015 ppm mol to 100 ppm mol with respect to 1 mol of the compound represented by the formula (a1) or (a2), and wherein the condition (2) is that a molar ratio represented by the phosphorous compound (mol)/the metal (mol) is 150 or more, (a1)

(a2)

wherein, in the formula (a1), X represents a hydrogen atom, a cyano group, an aldehyde group or —CH=NR group, and R represents a hydrogen atom, an alkyl group having 1 to 6 carbon atoms or an aryl group; in the formula (a1) and the formula (a2), n represents 0, 1 or 2, and wherein aldehyde compounds represented by the following formula (b1) or the following formula (b2);

(b1)

(b2)

wherein n and X are previously described (c1)

(c2)

wherein n is previously described, (d1)

(d2)

wherein n is previously described, and wherein the step (a) further satisfies the condition (3) in which is that a molar ratio of "the phosphorous compound (mol)" to "the compound (mol) represented by the formula (a1) or (a2)" is 0.003 to 0.05.

15. The process for producing the isocyanate compound according to claim 14, wherein the compound containing a metal belonging to Groups 8 to 10 is a rhodium compound, a cobalt compound, a ruthenium compound or an iron compound.

16. The process for producing the isocyanate compound according to claim 14,
   wherein the compound containing a metal belonging to Groups 8 to 10 is a rhodium compound.

17. The process for producing the isocyanate compound according to claim 14,
   wherein the compound represented by the formula (a1) is used, and that compound is represented by the following formula (1)

(1)

wherein, in the formula (1), X is the same as in the formula (a1).

* * * * *